United States Patent [19]
Clark et al.

[11] Patent Number: 5,603,727
[45] Date of Patent: Feb. 18, 1997

[54] THERMAL PACK WITH INTERRELATED COMPARTMENTS

[76] Inventors: Donald W. Clark; Jill Clark, both of 1512 W. Ileso Cir., Mesa, Ariz. 85202

[21] Appl. No.: 567,194

[22] Filed: Dec. 5, 1995

[51] Int. Cl.[6] .................................................... A61F 7/00
[52] U.S. Cl. .......................... 607/108; 607/114; 126/204; 165/46
[58] Field of Search ................................... 206/219, 221, 206/469; 607/96, 108–112, 114; 383/901; 273/18 R; 165/46; 126/204

[56] References Cited

U.S. PATENT DOCUMENTS

| | | | |
|---|---|---|---|
| 3,900,035 | 8/1975 | Welch et al. | 128/402 |
| 4,972,832 | 11/1990 | Trapini et al. | 128/402 |
| 5,129,391 | 7/1992 | Brodsky et al. | 607/110 |
| 5,184,613 | 2/1993 | Mintz | 128/402 |
| 5,190,033 | 3/1993 | Johnson | 128/403 |
| 5,305,471 | 4/1994 | Steele et al. | 2/102 |
| 5,366,491 | 11/1994 | Ingram et al. | 607/108 |
| 5,375,278 | 12/1994 | VanWinkle et al. | 5/644 |
| 5,383,921 | 1/1995 | Barry | 607/114 |
| 5,476,492 | 12/1995 | Unrug | 607/114 |

*Primary Examiner*—Angela D. Sykes
*Assistant Examiner*—Robert L. Nasser, Jr.
*Attorney, Agent, or Firm*—Schmeiser, Olsen & Watts

[57] ABSTRACT

A thermal packet having temperature retaining particles movable within the packet. A plurality of barriers located within the packet form migration paths and retaining areas to facilitate the use of the packet on various body areas.

6 Claims, 2 Drawing Sheets

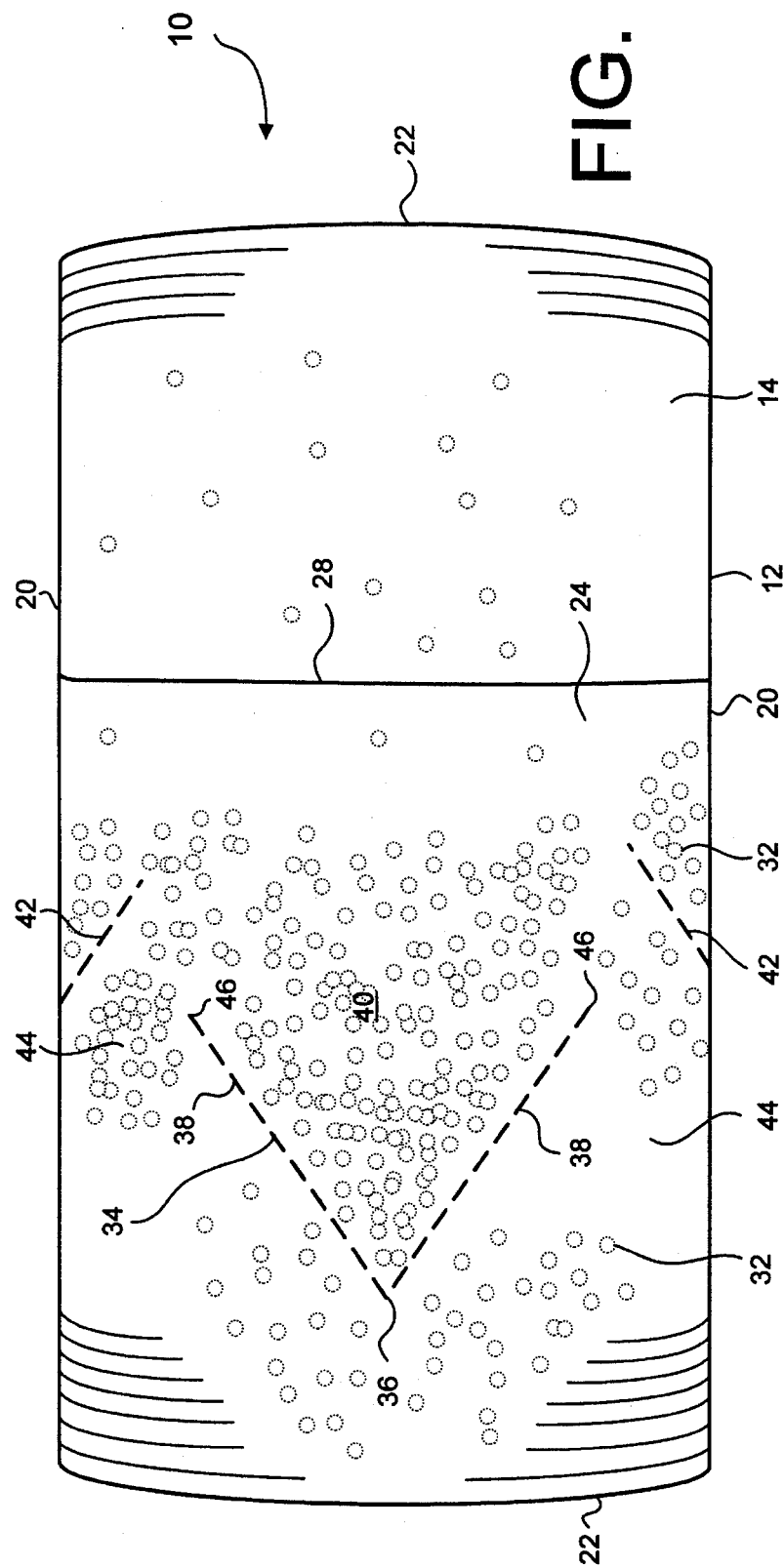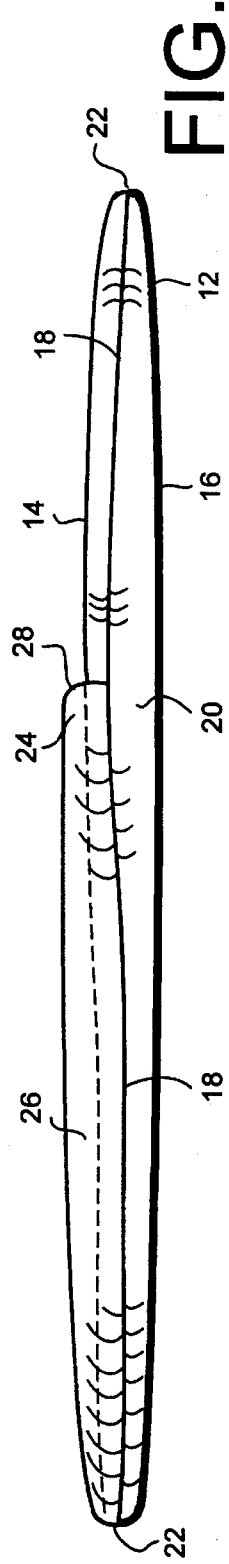

THERMAL PACK WITH INTERRELATED COMPARTMENTS

FIELD OF THE INVENTION

Generally, this invention relates to thermal packs. More specifically, this invention is a thermal pack which contains a natural temperature retaining material such as corn and has barriers and communicating compartments for easily locating the temperature retaining materials in the desired areas.

BACKGROUND OF THE INVENTION

Numerous injuries and physical problems can be alleviated through the application of heat or cold. To accomplish these treatments many devices have been developed which facilitate these applications. Early versions of these devices took the form of ice bags and hot water bottles. However, as technology has advanced, variations have been made to these items to enhance their effectiveness.

These enhancements generally take one of two forms. In the first, the heat and/or cold retaining material is modified often to either obtain better temperature transfer and/or to retain the temperature for an extended period of time.

For example, the patent to Van Winkle et al., U.S. Pat. No. 5,375,278, discloses a natural temperature retaining material such as barley or seeds with a preferred water content.

U.S. Pat. No. 5,366,491, issued to Ingram et al., discloses a monitoring device which serves as a warning system to prevent the application of a thermal pack wherein the temperature is so different from the body temperature as to be detrimental.

The second type of modification relates to the shaping of the thermal pack itself for better application to a person's body. For example, the patent to Steele, U.S. Pat. No. 5,305,471, shows an insulated cooling vest having a number of compartments for receiving thermal packs.

The patent to Welsh et al., U.S. Pat. No. 3,900,035, discloses an elastic bandage which is particularly adapted to fit over joint areas, and the patent to Mintz, U.S. Pat. No. 5,184,613, discloses a thermal pack structure which is particularly suited for infants.

Combining both of these objectives, the patent to Johnson, U.S. Pat. No. 5,190,033, which alters the thermal material by using hollow capsules filled with cold/hot storing fluids. In addition, the Johnson patent utilizes a plurality of partitions to prevent the migration of these capsules within the thermal pack, as well as a screen plug which permits air to be expelled from the pouch.

Thus, while most of the prior art has been concerned with either the materials within the thermal pack or the use of separate compartments for preventing migration, little, if any, attention has been paid to the possibility of utilizing the migration of the materials within the pack to provide the pack with greater versatility when being applied to different parts of the body. Versatility in application is generally sought, either as in the Steele et al. patent by using different pockets into which thermal packs can be inserted or as in Trapini et al., U.S. Pat. No. 4,972,832, where the pack may be folded to conform better to various body pans. Such an approach, however, is undesirable for certain applications. For example, in order to obtain different shapes for conforming to various body pans the structure of the Trapini pack is generally complex. While this is most likely not a problem where the pack is being used by an experienced trainer or coach, an individual who only uses the pack occasionally could have difficulties. Accordingly, it may not only be confusing to use, and generally the cost of manufacturing is significant. In the Steele patent the item is bulky and not easy to carry around, as one must have not only the jacket, but also a supply of packs to insert into the desired areas.

SUMMARY OF THE INVENTION

Accordingly, it is an object of this invention to provide a cost efficient thermal pack which may be easily adapted to treat various parts of the body.

A further object of this invention is to provide a thermal pack which is inexpensive to manufacture and environmentally save.

It is a further object of the invention to provide a thermal pack which also has a soothing effect on one's olfactory senses.

Yet a further object of the subject invention is to provide a thermal pack that conforms well to the treated area.

Other objects and attributes of the subject invention will become evident as one works with the invention and considers the following descriptions of the invention.

The subject invention utilizes the migrational tendencies of the material within the thermal pack to an advantage. This is done by forming barriers which facilitate the movement of the thermal material of from one end of the pack to the other, while inhibiting and capturing in partial pockets the thermal material as it is moved back toward the first end of the pack. In addition, channels within the pack narrow from one end to the other which causes a bunching of the thermal material which aids in heat retention while allowing variations in pack configuration which can be changed depending on the part of the body to be treated.

For ease in production the barriers, which facilitate the movement of the thermal material from one end to the other, also aid in the initial manufacture of the item. Thus, the thermal material can be added from that side wherefrom the movement of the material is facilitated, thus, making the loading of the thermal material much easier. Furthermore, prior to sealing the pack the fact that the barriers inhibit the migration of the thermal material back toward the opening makes it easier to maneuver the pack during sewing without having the thermal material fall out.

Once the pack is sealed and ready for use, the thermal material may be either heated or cooled depending on the appropriate treatment. In this regard, the barrier structure within the pack facilitates the bunching of thermal material at different locations. The bunching of material provides a greater mass which helps maintain the temperature of the material. Furthermore, depending upon the body part to be treated, the thermal material may be located in different areas of the pack, again facilitated by the barriers, in order to apply the treatment into the right areas.

Furthermore, an open compartment on the outside of the pack allows one to insert a body part which not only helps to locate the body part relative to the thermal material and allow movement without moving the pack, but also forms a temperature pocket so that the heat or cold affects to a lesser degree the areas about the injury. These features taken alone and in combination allow the user to easily apply the proper treatment to the desired areas.

For example, if one injured the inside and bottom of the right foot and wished to apply heat, one would move the bag to facilitate the flow of the thermal material into those portions of the bag which will correspond to the injured areas. This would be accomplished by lifting one side of the bag causing the thermal material to flow to the other side and then raising the end of the bag which would facilitate the movement of the thermal material toward the other end. However, because of the narrowing of the channel along the sides of the bag some of the material would bunch together at one side of the bag. Then, by simply holding the bag so as to retain the thermal material in the narrowing sleeve one would simply tilt the other end of the bag causing the thermal material to flow into the central pocket. Inserting the right foot into the compartment formed over the bag would result in the thermal material in the pocket being applied to the bottom of the foot while the thermal material bunched in the sleeve on the left side would be applied to the inside of the foot. Thus, the appropriate treatment would be applied to the right areas while the surrounding areas would not be directly treated to any significant degree except for the general warmth which would develop in the pocket.

Similarly, if one wished to treat only the bottom of a body part, virtually all of the thermal material could be located within the pocket. Conversely, if the right side of a body part were to be treated, one could bunch the thermal material in the narrowing right sleeve. Finally, if a general treatment was desired without any specific location, one could simply spread the thermal material out within the pack and, pressing down on the packet to form a relatively consistent thermal layer which could generally be applied to or around the desired area.

As will be shown in greater detail hereafter, these purposes are generally accomplished through the use of an arrow or chevron shaped barrier centrally located in the pack and having wings extending outwardly toward the sides of the pack. The benefit of the chevron may enhanced by additional barriers on each side of the pack which assist in the flow of material to the inside of the chevron as opposed to flowing around the chevron.

One desirable feature to further enhance the overall treatment includes treating the thermal material with a particular scent which can have a soothing effect on the user. while the scent provides an overall benefit by creating a more pleasant atmosphere, it does not significantly affect the actual functioning of the pack vis-a-vis its application to and treatment of a particular injury or body area.

BRIEF DESCRIPTION OF THE DRAWINGS

FIG. 1 is a top plane view of the invention;

FIG. 2 is a side elevational view of the invention; and

DETAILED DESCRIPTION OF THE DRAWINGS

Figure 3:
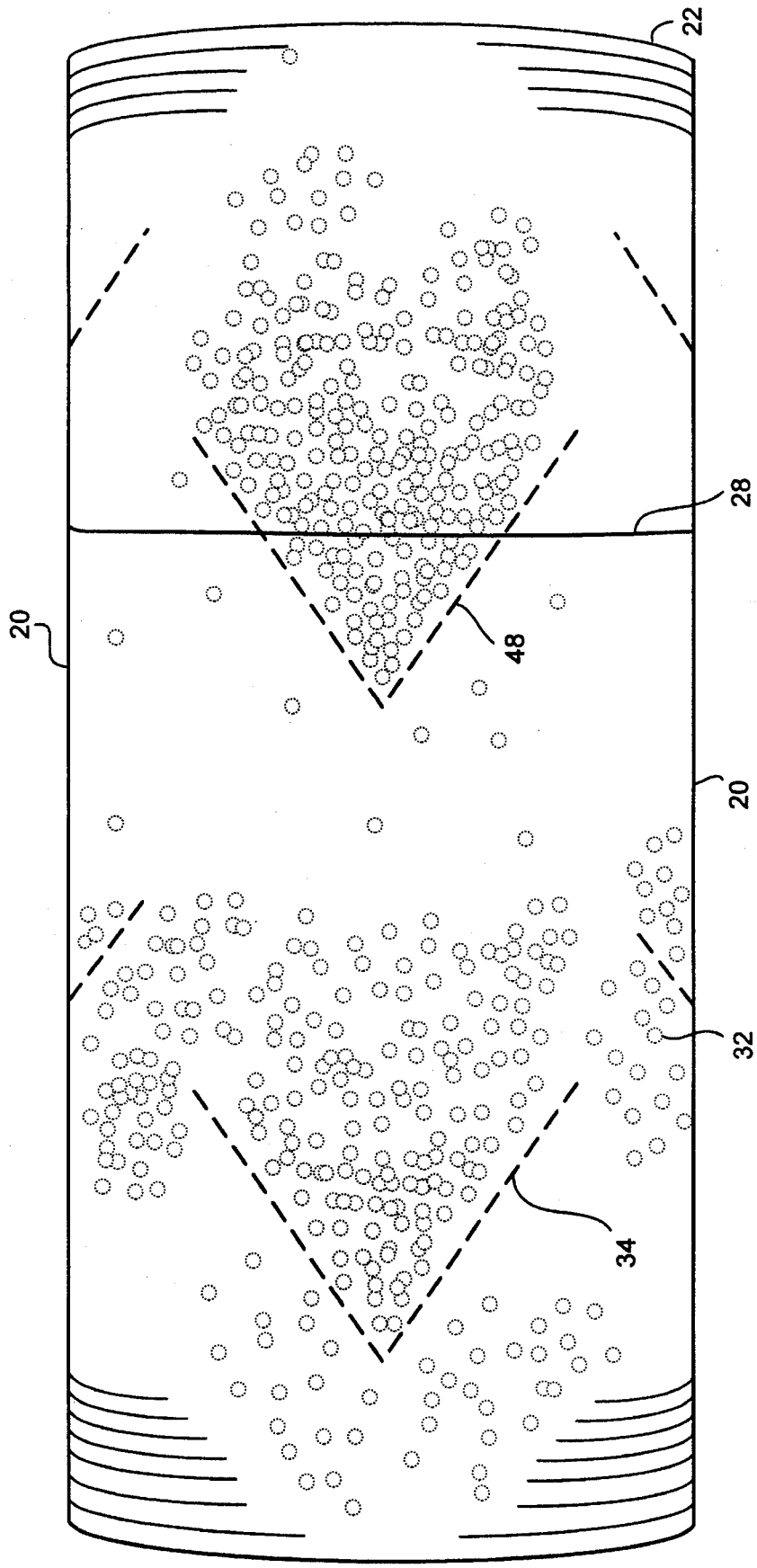
FIG. 3 is a top plane view of an alternate embodiment.

FIG. 1 discloses the thermal pack generally designated as 10. The pack 10 has a pliable container 12 which may be made from any suitable material which is not only pliable, but durable. In our preferred embodiment, the material of choice is muslin. The container 12 has a top surface 14 and a bottom surface 16.

As shown in FIG. 2 the top and bottom surfaces are connected about their periphery 18 forming opposing side walls 20 and end walls 22 a covering 24 is secured over a portion of the top surface 14 forming a compartment 26 which is sealed along three sides by being sewn to the outer peripheries of the top and bottom surfaces and is open at the side which extends across the container at 28.

The container 12 defines an interior space in which are located heat retaining particles 32 which in the preferred embodiment is recleaned animal feed corn.

By sewing the top surface 14 and the bottom surface 16 together at various points barriers may be formed. The first chevron or arrow shaped barrier 34 has a point 36 which is located towards one of the end walls 22. Angled backwardly from the point towards the side walls 20 are wings 38. Between the wings 38 a pocket 40 is formed which through the manipulation of the heat retaining particles 32 can be a catch area for the particles.

The chevron barrier 34 has its point located substantially in the center of the container 12. Thus, heat retaining particles 32 may be put into the bag at the end wall 22 which is closest to the point 36, thus facilitating the loading of the particles 32 into the container 12.

Second barriers 42 extend outwardly from the side wall toward the center of the bag in the same general direction as the wings 38. The second barriers 42 block the straight line flow of particles past the chevron 34.

The portion of the container between the wings 38 and their closest side walls 20 form a narrowing sleeves 44 with the narrowest portion of the sleeves being between the wing ends 46 and the side walls 20.

In a preferred embodiment, the pack is approximately twelve inches in length and seven inches in width with the wings of the chevron being approximately five inches and the angle between the wings being between forty-five and seventy degrees.

As shown in FIG. 3 there is an alternate embodiment including a second chevron 48. The second chevron 48 is aligned in the same direction as the first chevron 34, but is set further back in the thermal pack. In the preferred embodiment approximately half of the second chevron 48 lies under the compartment 26 while the other half lies outside the compartment as shown in FIG. 2. This allows for the location of heat retaining particles 32 within the pocket formed by the second chevron 48 and aids in the application of those particles to body areas that cannot be slipped into the compartment.

While the above describes the embodiment of the subject invention, it should be appreciated that numerous variations may be made without deviating from the essence of the invention which is intended to be limited only by the appended claims.

We claim:

1. A thermal pack for application to the body comprising:

a pliable container having a top surface and a bottom surface, said top and bottom surfaces being connected to each other about their periphery thereby forming opposing side walls and opposing end walls, said container enclosing an interior space;

heat retaining particles loosely confined for movement within the container;

a barrier within the container forming a pocket in said container into which particles may be directed, said barrier also forming at least one narrowing sleeve-like area between the barrier and one of the walls whereby said pocket and said sleeve are adjacent to each other, said barrier having one side which facilitates the passage of the particles into the sleeve for movement past the barrier and a second side which forms a catch for retaining particles within the pocket whereby lifting one end wall above its opposing end wall will cause particles to flow through the sleeve area and congregate opposite the pocket opening, and then lifting the opposing wall will cause a plurality of particles to flow into the pocket, said barrier being chevron shaped, having a point located centrally between the side walls and toward one of the end walls, and wings angling backward from said point, the space between the wings forming the pocket, said wings angling toward the sidewalls forming said narrowing sleeve whereby said chevron directs particles into said sleeve, and a second barrier extending outwardly from a sidewall in the same general direction as the wings, said sidewall at least partially blocking the straight line flow of particles back through the narrowest part of the sleeve and to the end of the container toward the point.

2. The invention of claim 1 wherein the heat retaining particles is recleaned animal feed corn.

3. The invention of claim 2 wherein the pack is scented.

4. A thermal pack for application to the body comprising:

a pliable container having a top surface and a bottom surface, said top and bottom surfaces being connected to each other about their periphery thereby forming opposing side walls and opposing end walls, said container enclosing an interior space;

heat retaining particles loosely confined for movement within the container;

a barrier within the container forming a pocket in said container into which particles may be directed, said barrier also forming at least one narrowing sleeve-like area between the barrier and one of the walls whereby said pocket and said sleeve are adjacent to each other; and a covering over the outer side of the top surface forming a compartment which extends substantially over the pocket area, whereby particles congregated within the pocket are covered, said compartment being partially open to allow for the insertion of an area to be treated.

5. The invention of claim 4 further comprising a second chevron shaped barrier within the container.

6. The invention of claim 5 wherein the barriers are formed by sewing portions of the top and bottom surfaces of the container together.

* * * * *